United States Patent
Feiler

Patent Number: 5,900,490
Date of Patent: May 4, 1999

[54] PREPARATION OF PERYLENE-3, 4-DICARBOXYLIC ACID ANHYDRIDES

[75] Inventor: Leonhard Feiler, Givisiez, Switzerland

[73] Assignee: Ciba Specialty Chemicals Corporation, Tarrytown, N.Y.

[21] Appl. No.: 09/007,193

[22] Filed: Jan. 14, 1998

[30] Foreign Application Priority Data

Jan. 14, 1997 [DE] Germany .............................. 19701009

[51] Int. Cl.$^6$ .................................................. C07D 311/78
[52] U.S. Cl. .............................. 549/232; 548/417; 549/31
[58] Field of Search ............................................. 549/232

[56] References Cited

U.S. PATENT DOCUMENTS

| | | | |
|---|---|---|---|
| 4,650,879 | 3/1987 | Spietschka et al. | 549/232 |
| 5,650,513 | 7/1997 | Langhals et al. | 546/38 |

FOREIGN PATENT DOCUMENTS 9622331  7/1996  WIPO .

OTHER PUBLICATIONS

Mol. Cryst. Liq. Cryst., 1988, vol. 158B, pp. 337–352.

Bulletin of the Chemical Society of Japan, vol. 52, (6), pp. 1723–1726 (1979).

*Primary Examiner*—Bernard Dentz
*Attorney, Agent, or Firm*—Kevin T. Mansfield; Jacob M. Levine

[57] ABSTRACT

Preparation of perylene-3,4-dicarboxylic acid anhydrides of the general formula I

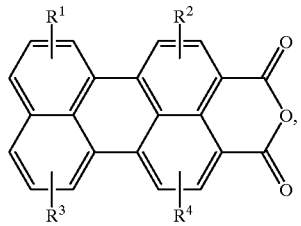

wherein $R^1$, $R^2$, $R^3$ and $R^4$ can each be independently of one another hydrogen, halogen, $C_1$–$C_{20}$alkyl, $C_3$–$C_{14}$cycloalkyl, $C_1$–$C_{20}$alkoxy, phenyl, phenyloxy or phenylthio, where phenyl can in each case be mono- or polysubstituted by halogen, $C_1$–$C_{20}$alkyl, $C_3$–$C_{14}$cycloalkyl and/or $C_1$–$C_{20}$alkoxy; —$NR^5_2$ or —$OR^5$, wherein $R^5$ is hydrogen or $C_1$–$C_{20}$alkyl, or one of the pairs $R^1/R^2$ and $R^3/R^4$ each in 6,7- or 1,12-position is a bridge having the bridge atoms or bridge atom groups —O—, —S—, S=O, $SO_2$ or —$NR^6$, wherein $R^6$ is hydrogen, $C_1$–$C_{20}$alkyl or $C_3$–$C_{14}$cycloalkyl, by treating a perylene-3,4-dicarboximide of formula II

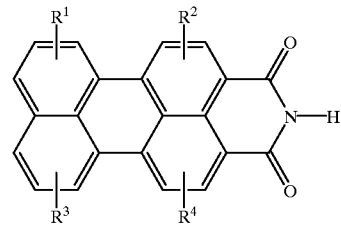

(a) in a first step with a base and,
(b) in a second step, reacting the resultant anion with an alkylation agent $R^7$—X, X being halogen and $R^7$ being unsubstituted or phenyl-substituted $C_1$–$C_{20}$alkyl, to the corresponding carboximide and,
(c) in a third step, treating the alkylated carboximide first with a base and, after the treatment with a base, obtaining the perylene-3,4-dicarboxylic acid anhydride I by acidifying the reaction mixture, and novel perylene-3,4-dicarboxylic acid anhydrides, novel N-alkylperylene-3,4-dicarboxylic acid imides and possibilities for the application of the compounds prepared according to this invention.

4 Claims, No Drawings

PREPARATION OF PERYLENE-3, 4-DICARBOXYLIC ACID ANHYDRIDES

The present invention relates to an improved process for the preparation of perylene-3,4-dicarboxylic acid anhydrides of the general formula I

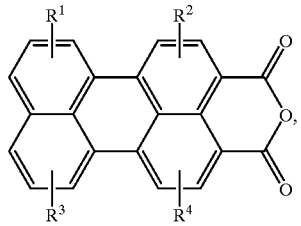

wherein $R^1$, $R^2$, $R^3$ and $R^4$ can each be independently of one another hydrogen, halogen, $C_1$–$C_{20}$alkyl, $C_3$–$C_{14}$cycloalkyl, $C_1$–$C_{20}$alkoxy, phenyl, phenyloxy or phenylthio, where phenyl can in each case be mono- or polysubstituted by halogen, $C_1$–$C_{20}$alkyl, $C_3$–$C_{14}$cycloalkyl and/or $C_1$–$C_{20}$alkoxy; —$NR^5{}_2$ or —$OR^5$, wherein $R^5$ is hydrogen or $C_1$–$C_{20}$alkyl, or one of the pairs $R^1/R^2$ $^{and}$ $^{R3}/R^4$ each in 6,7- or 1,12-position is a bridge having the bridge atoms or bridge atom groups —O—, —S—, S=O, $SO_2$ or —$NR_6$, wherein $R^6$ is hydrogen, $C_1$–$C_{20}$alkyl or $C_3$–$C_{14}$cycloalkyl.

Processes for the preparation of perylene-3,4-dicarboxylic acid anhydrides are known. Mol.Cryst.Liqu.Cryst., 158b, (1988), p. 337 et seq., inter alia, describes a process in which perylene-3,4:9.10-tetracarboxylic acid bisanhydride is converted to perylene-3,4-dicarboxylic acid anhydride by gas phase decarboxylation. However, owing to its low yield (~5%) this procedure is not important in practice.

Another possible starting product for the preparation of perylene-3,4-dicarboxylic acid anhydrides is the technically easily accessible perylene-3,4-dicarboximide. However, direct saponification of perylene-3,4-dicarboximides with bases is impossible because the carboximide nitrogen is deprotonised and an imide anion is obtained which is inert against bases such as alkalis.

However, it is possible to carry out saponification with concentrated sulfuric acid by the method described in Bull. Chem. Soc. Jpn. 52 (1979) p. 1723 et seq.. Starting from perylene-3,4-dicarboximide, which is then heated in concentrated sulfuric acid to about 250° C., sulfonated perylene-3,4-dicarboxylic acid anhydride is obtained. However, the authors have not isolated this intermediate, but have further reacted it with amines to perylene-3,4-dicarboximide sulfonic acids which are substituted at the nitrogen atom and which are subsequently desulfonised to obtain the corresponding perylene-3,4-dicarboximides which are substituted at the nitrogen atom. A further disadvantage besides the elaborate way in which the reaction is carried out under drastic conditions (conc. $H_2SO_4$ at 250° C.) is that the perylene-3,4-dicarboximide yields are only moderate.

By another process, known from DE-A 4,338,784, N-(2,5-di-tert-butylphenyl)perylene-3,4-dicarboximide is prepared in a first step starting from perylene-3,4:9,10-tetracarboxylic acid bisanhydride. After being purified, it is converted to perylene-3,4-dicarboxylic acid anhydride by treatment with alkali. This process has the disadvantage that the N-(2,5-di-tert-butyl-phenyl)perylene-3,4-dicarboximide must be purified by chromatography and that the end product is obtained in a total yield of only 37%, based on perylene-3,4:9,10-tetracarboxylic acid bisanhydride.

WO 96/22331 discloses perylene-3,4-dicarboxylic acid imides as well as a process for their preparation by reacting a perylene-3,4:9,10-tetracarboxylic acid with a primary amine in the presence of a tertiary nitrogenous base compound as solvent and a transition metal as catalyst.

Accordingly, it is the object of this invention to provide an improved process for the preparation of perylene-3,4-dicarboxylic acid anhydrides which does not have the above-mentioned disadvantages. In particular, it should be possible to produce higher yields of perylene-3,4-dicarboxylic acid anhydrides starting from perylene-3,4-dicarboximide and/or its derivatives by a technically simpler process. In addition, a process for the preparation of high yields of perylene-3,4-dicarboxylic acid imides should be provided in which no transition metal catalyst should be used.

Accordingly, the novel process has been found for the preparation of perylene-3,4-dicarboxylic acid anhydrides of the general formula I

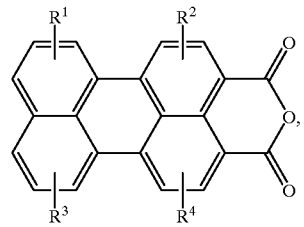

wherein $R^1$, $R^2$, $R^3$ and $R^4$ can each be independently of one another hydrogen, halogen, $C_1$–$C_{20}$alkyl, $C_3$–$C_{14}$cycloalkyl, $C_1$–$C_{20}$alkoxy, phenyl, phenyloxy or phenylthio, where phenyl can in each case be mono- or polysubstituted by halogen, $C_1$–$C_{20}$alkyl, $C_3$–$C_{14}$cycloalkyl and/or $C_1$–$C_{20}$alkoxy; —$NR^5{}_2$ or —$OR^5$, wherein $R^5$ is hydrogen or $C_1$–$C_{20}$alkyl, or one of the pairs $R^1/R^2$ and $R^3/R^4$ each in 6,7- or 1,12-position is a bridge having bridge atoms or bridge atom groups —O—, —S—, S=O, $SO_2$ or —$NR^6$, wherein $R^6$ is hydrogen, $C_1$–$C_{20}$alkyl or $C_3$–$C_{14}$cycloalkyl, by treating a perylene-3,4-dicarboximide of formula II

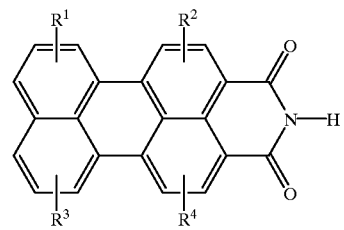

(a) in a first step with a base and, (b) in a second step, reacting the resultant anion with an alkylation agent $R^7$—X, X being halogen and $R^7$ being unsubstituted or phenyl-substituted $C_1$–$C_{20}$alkyl, to the corresponding carboximide and, (c) in a third step, treating the alkylated carboximide first with a base and, after the treatment with a base, obtaining the perylene-3,4-dicarboxylic acid anhydride I by acidifying the reaction mixture.

There have also been found novel perylene-3,4-dicarboxylic acid anhydrides, novel N-alkyl-perylene-3,4-dicarboxylic acid imides as well as possibilities for the application of the compounds prepared according to this invention.

The treatment of carboximide II with a base in the first step (a) is usually carried out in the temperature range from 0 to 250° C., preferably at room temperature and, if desired, in the presence of a solvent.

Suitable bases are usually alcoholates or hydroxides of alkali metals and alkaline earth metals. In this case the base should conveniently be chosen such that the hydrogen atom at the imide nitrogen atom can also be removed. A carboximide anion is then obtained. Alcoholates may be, for example, alkali metal salts of $C_1$–$C_4$alkanols, typically sodium methylate, potassium methylate, sodium ethylate or potassium ethylate. Suitable alkali metal hydroxides or alkaline earth metal hydroxides are, for example, sodium hydroxide and potassium hydroxide. Sodium methylate or potassium hydroxide are particularly preferred.

The molar ratio of dicarboximide 11 to base is usually chosen in the range from 1:1 to 0.01:1, preferably from 0.33:1 to 0.5:1 .

When using hydroxides, such as potassium hydroxide, suitable solvents are aprotic polar solvents, typically dimethyl sulfoxide ("DMSO") or N-methylpyrrolidone ("NMP"), and when using alcoholates, suitable solvents are the corresponding alcohols, i.e. when using sodium methylate preferably methanol, etc. According to findings so far, the amount of solvent used is uncritical and can be chosen, for example, in the range from 100:1 to 0.1:1 (solvent to dicarboximide II, by weight).

The solvent is preferably distilled off after the reaction is complete. However, the solvent may also remain in the reaction mixture.

The duration of the reaction usually depends essentially on the reaction temperature, which is usually chosen in the range of 0.5 to 10 h.

Accordingly to, inter alia, DE-C 486,491, the dicarboximide II ($R^1$ to $R^4$=hydrogen) used as starting material is usually industrially obtainable by reacting the perylene-3,4-dicarboxylic acid anhydride-9,10-dicarboximide obtainable from perylene-3,4:9,10-tetracarboxylic acid bisanhydride with potash lye. The substituted dicarboximides II can be prepared in analogy to the process described in DE-A 4,338,784. Nitro derivatives, for example, are obtainable by nitration with dinitrogen tetraoxide in dichloromethane or with copper nitrate in acetic anhydride. The corresponding amino compounds can be synthesised by reducing the nitro compounds, and these amino compounds can in turn be derivatised. Bromated derivatives can be prepared, for example, in analogy to DE-A 4,338,784 by direct bromation; the corresponding alkoxy and phenoxy derivatives can usually be obtained therefrom by nucleophilic substitution. Alkyl derivatives are obtainable in analogy to Leonhard Feiler, Dissertation 1995, University of Munich, by direct alkylation using alkyl lithium compounds.

In the second reaction step (b) of this invention, the anion of the perylene-3,4-dicarboximide II is reacted with the alkylation agent $R^7$—X.

X is halogen, typically chloro, bromo or iodo, preferably bromo or iodo, and $R^7$ is unsubstituted or phenyl-substituted $C_1$–$C_{20}$alkyl.

$C_1$–$C_{20}$Alkyl is, for example, methyl, ethyl, n-propyl, isopropyl, n-butyl, sec-butyl, i-butyl, tert-butyl, n-amyl, tert-amyl, hexyl, heptyl, octyl, 2-ethylhexyl, nonyl, decyl, dodecyl, tetradecyl, hexadecyl, octadecyl, nonadecyl or eicosyl, preferably $C_1$–$C_6$alkyl, such as methyl, ethyl, n-propyl, isopropyl, n-butyl, sec-butyl, i-butyl, tert-butyl, n-amyl, tert-amyl, hexyl.

Where phenyl group-substituted alkyl is used, it is preferred to choose $C_1$–$C_4$alkyl which is monosubstituted by phenyl, for example benzyl, phenylethyl, phenylpropyl or phenylbutyl, particularly preferably benzyl.

Particularly preferred alkylation agents are dimethyl sulfate, $C_1$–$C_6$alkyl bromides or $C_1$–$C_6$-alkyl iodides, such as methyl bromide, methyl iodide, ethyl bromide, ethyl iodide, and benzyl chloride.

The molar ratio of dicarboximide II to alkylation agent is usually chosen in the range from 1:1 to 1:10, preferably from 1:1 to 1:4.

If desired, the alkylation reaction can be carried out in a solvent, preferably in an inert aprotic polar solvent such as N-methylpyrrolidone or dimethyl sulfoxide. The amount of solvent used is usually uncritical and is normally in the range from 250:1 to 0.1:1 (amount of solvent to amount of dicarboximide II originally used).

The reaction temperature is usually chosen in the range from 0 to 150, preferably from 20 to 130° C. In the case of, in particular, non-eliminating alkylation agents, such as benzyl chloride or dimethyl sulfate, a higher temperature range is preferably chosen, whereas a lower reaction temperature is preferably chosen in the case of higher alkylation agents, such as octyl bromide, and of low-boiling alkylation agents, such as methyl iodide and ethyl bromide.

The duration of the reaction usually depends essentially on the chosen reaction temperature and on the reactivity of the reactants; it is usually chosen in the range from 0.3 to 18 h.

In a preferred embodiment of this invention, the solvent is distilled off together with the unreacted alkylation agent after alkylation is complete. The separated and, if desired, purified solvent can be recycled.

In the third reaction step (c) of this invention, the N-alkylperylene-3,4-dicarboximide obtained in the second step (b) is treated first with a base, and the desired perylene-3,4-dicarboxylic acid anhydride I is then obtained by acidifying the reaction mixture.

The base used in step (c) is preferably an alkali metal hydroxide or alkaline earth metal hydroxide in a primary, secondary or tertiary alcohol of no more than 8 carbon atoms.

Illustrative examples of alkali metal hydroxides or alkaline earth metal hydroxides are lithium hydroxide, sodium hydroxide, potassium hydroxide, magnesium hydroxide and calcium hydroxide. Potassium hydroxide is particularly preferred.

The molar ratio of N-alkyldicarboximide to base is preferably chosen in the range from 1:2 to 1:25, more preferably from 1:15 to 1:20.

The following alcohols are to be mentioned as examples of solvents: primary $C_1$–$C_8$-alkanols, such as methanol, ethanol, n-propanol, n-butanol, i-butanol, n-pentanol, n-hexanol, n-heptanol and n-octanol; secondary $C_3$–$C_8$alkanols, such as i-propanol, sec-butanol, i-pentanol, i-hexanol, i-heptanol and i-octanol; tertiary $C_4$–$C_8$alkanols, such as tert-butanol, tert-amyl alcohol, tert-hexanol, tert-heptanol and tert-octanol.

The amount of solvent is usually chosen in the range from 25 to 250, preferably from 70 to 100 ml, of solvent per gram of N-alkyldicarboximide.

The solvent is usually removed by distillation at the end of the reaction. If desired, it can be purified and recycled. The reaction temperature is usually chosen in the range from 20 to 250, preferably from 30 to 100° C.

The duration of the reaction usually depends on the chosen reaction temperature and on the reactivity of the reactants and is usually in the range from 0.5 to 10 h.

In a particularly preferred embodiment of this invention, saponification is carried out using potassium hydroxide in tert-butanol.

According to this invention, the perylene-3,4-dicarboxylic acid di-salt is converted to the corresponding perylene-3,4-dicarboxylic acid anhydride by acidification.

For acidification it is possible to use all suitable acids customarily used for neutralisation, for example mineral acids or organic acids. Illustrative examples are: sulfuric acid, hydrochloric acid, nitric acid, phosphoric acid and acetic acid.

The amount of acid used usually depends onits concentration and acid strength and is usually chosen such that at the end of the neutralisation the reaction mixture has a pH in the range from 6.5 to 7.5.

The desired anhydride I is usually isolated after neutralisation by customary measures such as filtering or by removing the solvent by distillation. The crude product so obtained is preferably purified by washing with water, if desired with water in the temperature range from 40 to 98° C. ("hot water") and subsequently dried, preferably under reduced pressure (created, for example, by using a water-jet pump or another conventional vacuum pump).

In a preferred embodiment of this invention, the perylene-3,4-anhydride I obtained is treated with a weak base in aqueous medium, usually resulting in the corresponding perylene-3,4-dicarboxylic acid di-salt which dissolves. The insoluble components such as perylene-3,4-dicarboximide and/or N-alkylperylene-3,4-dicarboximides can be separated by customary measures such as filtration or centrifugation and can then be used as starting material, if desired.

After separating the insoluble components, the dissolved di-salt is acidified with a moderately weak or strong acid, for example with one of the above-mentioned acids, normally affording the inventive perylene-3,4-dicarboxylic acid anhydride in good purity after separation by e.g filtration and subsequent drying.

Suitable weak bases are in this case alkali metal carbonates such as sodium carbonate and potassium carbonate, preferably potassium carbonate. The crude product is preferably heated in an aqueous alkali metal carbonate solution to boiling until the desired product is dissolved, and after separation by, preferably, filtration the filter residue is washed with water of 40 to 98° C. until the filtrate runs colourless.

The perylene-3,4-dicarboxylic acid anhydride so obtained is usually pure enough for chemical reactions. Higher purities can be achieved, for example, by extractive recrystallisation with an aromatic hydrocarbon such as toluene.

This invention also relates to the intermediates of formula III

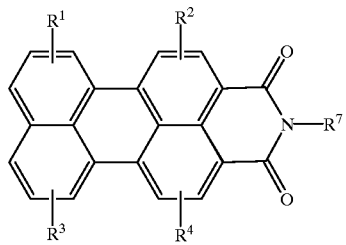

III which are obtained by the first two process steps (a) and (b) of the inventive process, wherein $R^1$ to $R^7$ are as defined above. Excepted are, however, those compounds wherein $R^1$ to $R^4$ are simultaneously hydrogen, and those compounds wherein $R^2$ is —$NH_2$ or —OH, $R^1$ and $R^3$ to $R^4$ are hydrogen, and $R^7$ is methyl, ethyl, propyl, butyl, hexyl and octyl, as well as those compounds wherein $R^2$ and $R^4$ are bromo, $R^1$ and $R^3$ are hydrogen, and $R^7$ is diisopropylphenyl.

In addition, this invention also relates to the perylene-3,4-dicarboxylic acid anhydrides I which are obtainable by the inventive process, in which $R^1$ to $R^4$ are not simultaneously hydrogen.

The novel perylene derivatives I and III are suitable for use as colourants, in particular as pigments and dyes, in general by methods known per se, preferably (a) for mass colouring polymers, where the polymers can be polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene or polyisoprene, or the copolymers of the cited monomers;

(b) as vat dyes or mordant dyes, for example for dyeing natural substances and, in particular, paper, wood, straw, leather, hides or natural fibre materials, such as cotton, wool, silk, jute, sisal, hemp, flax or animal hair (e.g. horsehair) and the conversion products thereof, such as viscose fibre, nitrate silk or cuprammonium rayon (rayon), preferred salts for mordanting being aluminium salts, chromium salts and iron salts;

(c) for the preparation of paints, paint systems, in particular automotive lacquers, coating compositions, paper colours, printing colours, inks, in particular for use in ink-jet printers, preferably in homogeneous solution as a fluorescent ink, and for painting and writing purposes, as well as in electrophotography, e.g. for dry copier systems (Xerox process) and laser printers;

(d) for security marking purposes, such as for cheques, cheque cards, currency notes, coupons, documents, identity papers and the like, where a special unmistakable colour impression is to be achieved;

(e) as an additive to colourants, such as pigments and dyes, where a specific colour shade is to be achieved, luminous shades being particularly preferred;

(f) for marking objects for machine recognition of these objects via the fluorescence, preferably for machine recognition of objects for sorting, e.g. including the recycling of plastics, alphanumerical prints or barcodes being preferably used;

(g) for converting the frequency of light, e.g. for turning short-wave light into long-wave visible light or for doubling or tripling the frequency of laser light in non-linear optics;

(h) for the production of passive display elements for a multitude of display, notice and marking purposes, e.g. passive display elements, notices and traffic signs, such as traffic lights;

(i) as starting material for supraconducting organic materials (via π-π-interaction, the addition of e.g. iodine usually resulting in a intermediary charge delocalisation);

(j) for marking with fluorescence in the solid state;

(k) for decorative and artistic purposes;

(l) for tracer purposes, e.g. in biochemistry, medicine, technology and natural science, where the novel colourants can be linked covalently to the substrates or via secondary valences, such as hydrogen bonds or hydrophobic interactions (adsorption);

(m) as fluorescent dyes in highly sensitive detection processes (see C. Aubert, J. Fünfschilling, 1. Zschokke- Gränacher and H. Langhals, Z. Analyt. Chem. 1985, 320, 361), in particular as fluorescent dyes in scintillators;

(n) as dyes or fluorescent dyes in optical light collection systems, in fluorescence solar collectors (see H. Langhals, Nachr. Chem. Tech. Lab. 1980, 28, 716), in fluorescence-activated displays (see W. Greubel and G. Baur, Elektronik 1977, 26, 6), in cold light sources used for light-induced polymerisation for the preparation of plastics, for testing of materials, for example in the production of semiconductor circuits, for analysing microstructures of integrated semiconductor components, in photoconductors, in photographic processes, in display, illumination or image converter systems, where excitation is effected by electrons, ions or UV radiation, e.g. in fluorescent displays, Braun tubes or in fluorescent lamps, as part of an integrated semiconductor circuit containing dyes as such or in combination with other semiconductors, for example in the form of an epitaxy, in chemiluminescence systems, e.g. in chemiluminescent flashlights, in luminescene immunoassays or other luminescence detection processes, as signal paints, preferably for visually emphasising strokes of writing and drawings or other graphic products, for marking signs and other objects for which a particular visual colour impression is to be achieved, in dye lasers, preferably as fluorescent dyes for generating laser beams, as optical recording medium and also as Q-switches;

(o) as rheology improvers and as dye component for dyeing metals by the ELOXAL process.

Advantages of the inventive process over the cited processes of the prior art are that it is technically simpler (one-pot process) and affords very good perylene-3,4-dicarboximide yields. Furthermore, elaborate purification operations are avoided.

In addition, the perylene derivatives I and III which can be prepared according to this invention are dyes or pigments having excellent fastness to light and, in some cases, strong fluorescence in the solid state, which cover almost the entire light spectrum from yellow to green.

Owing to the derivability of the novel anhydrides I by reaction with, for example, primary amines, they are also of interest for large-scale industrial production, it being possible to widely vary the physical properties of the compounds so obtained.

EXAMPLES

The preparation of perylene-3,4-dicarboximide is carried out in general analogy to the instructions described in DE-C 486,491 by suspending 3.00 g (7.67 mmol) of perylene-3, 4-dicarboximide-9,10-dicarboxylic acid anhydride together with 30 ml of 12% potash lye and heating this mixture for 18 h in an autoclave to 240 to 250° C. After cooling, the mixture is neutralised with conc. hydrochloric acid. The reddish-brown precipitate is collected by suction, washed repeatedly with distilled water and is then dried in a drying oven at 120° C. The perylene-3,4-dicarboximide so obtained can be used for reactions without further purification. Yield: 2.22 g (90%).

Example 1

1.60 g (5.2 mmol) of perylene-3,4-dicarboximide are suspended in 50 ml of abs. methanol and then 0.56 g (14.7 mmol) of sodium methylate is added and the mixture is stirred for 2 h at room temperature with the exclusion of moisture. After stripping off the methanol on a rotary evaporator, there are added 60 ml of N-methylpyrrolidone as solvent and 2.28 g (16.0 mmol) of methyl iodide, and this suspension is then stirred for 2 h at room temperature. After the reaction is complete, the N-methylpyrrolidone and excess methyl iodide are removed by distillation at reduced pressure.

The reddish-brown residue is then suspended in 150 ml of tert-butanol, charged with 6.0 g (107 mmol) of KOH pellets and boiled for 3 h, the colour of the mixture changing from reddish-brown to yellowish-brown. After the reaction is complete, the tert-butanol is removed by distillation and the residue is suspended in water and is slowly acidified with conc. hydrochloric acid. To make the resulting brown precipitate agglomerate, the mixture is boiled for some time. The precipitate is collected by suction and washed with hot water. The residue is boiled with 2N potassium carbonate solution and is then washed with hot water until the filtrate runs colourless. The residue consists of unreacted perylene-3,4-dicarboximide and small amounts of N-methyl-perylene-3,4-dicarboximide and can be recycled as starting product. The filtrate is acidified with hydrochloric acid and is then filtered, giving 1.20 g (75%) of brownish-red perylene-3,4-dicarboxylic acid anhydride.

IR (KBr): $\nu=1780$ cm$^{-1}$ (w), 1750 (m, C=O), 1725 (m, C=O), 1589 (s), 1568 (m), 1339 (m 1280 (s), 1130 (m), 1020 (m), 1002 (m), 860 (w), 843 (m), 812 (s), 767 (s), 740 (m).

Example 2

1.60 g (5.2 mmol) of perylene-3,4-dicarboximide are suspended in 50 ml of abs. methanol and then 0.56 g (14.7 mmol) of sodium methylate is added and the mixture is stirred at room temperature for 2 h with the exclusion of moisture. After stripping off the methanol on a rotary evaporator, there are added 60 ml of N-methylpyrrolidone as solvent and 2.04 g (16.1 mmol) of benzyl chloride, and this suspension is then stirred for 12 h at 50° C. After the reaction is complete, N-methylpyrrolidone and excess benzyl chloride are distilled off under vacuum.

The reddish-brown residue is suspended in 150 ml of tert-butanol and is then charged with 6.0 g (107 mmol) of KOH pellets and boiled for 3 h, the colour of the mixture changing from reddish-brown to yellowish-brown. After the reaction is complete, the tert-butanol is removed by distillation and the residue is suspended in water and slowly acidified with conc. hydrochloric acid. To make the resulting brown residue agglomerate, the mixture is boiled for some time. The residue is then collected by suction and washed with hot water. The residue is boiled with 2N potassium carbonate solution and is then washed with hot water until the filtrate runs colourless. The residue consists of unreacted perylene-3,4-dicarboximide and small amounts of N-benzyl-perylene-3,4-dicarboximide and can be recycled as starting product.

The filtrate is acidified with hydrochloric acid and is then filtered, giving 1.12 g (70%) of brownish-red perylene-3,4-dicarboxylic acid anhydride.

IR (KBr): $\nu=1780$ cm$^{-1}$ (w), 1750 (m, C=O), 1725 (m, C=O), 1589 (s), 1568 (m), 1339 (m) 1280 (s). 1130 (m), 1020 (m), 1002 (m), 860 (w), 843 (m), 812 (s), 767 (s), 740 (m).

Example 3

0.40 g (1.25 mmol) of perylene-3,4-dicarboximide is suspended in 25 ml of abs. methanol and then 0.17 g (1.9 mmol) of sodium methylate is added and the mixture is stirred for ½ h at room temperature with the exclusion of moisture. After removing the solvent by distillation, 20 ml of abs. N-methylpyrrolidone and 0.54 g (2.81 mmol) of 1-bromooctane are added and the mixture is stirred for 23 h at room temperature. After the reaction is complete, the N-methylpyrrolidone and excess 1-bromooctane are removed by distillation under vacuum.

The reddish-brown residue is then suspended in 60 ml of tert-butanol, charged with 1.5 g (22.8 mmol) of KOH pellets and boiled for 3 h, the colour of the mixture changing from reddish-brown to yellowish-brown. After the reaction is complete, the tert-butanol is removed by distillation, the residue is suspended in water and is slowly acidified with conc. hydrochloric acid. To make the resulting brown precipitate agglomerate, the mixture is boiled for some time. The precipitate is collected by suction and washed with hot water. The residue is boiled with 2N potassium carbonate solution and is then washed with hot water until the filtrate runs colourless. The residue consists of unreacted perylene-3,4-dicarboximide and small amounts of N-octylperylene-3,4-dicarboximide and can be recycled as starting product. The filtrate is acidified with hydrochloric acid and and is then filtered, giving 260 mg (65%) of brownish-red perylene-3,4-dicarboxylic acid anhydride. (The yield can be improved further if the residue is recycled as starting product.)

IR (KBr): $\nu$=1783 cm$^{-1}$ (w), 1753 (m, C=O), 1728 (m, C=O), 1592 (s), 1570 (m), 1501 (w), 1405 (w), 1372 (w), 1342 (m), 1285 (s), 1231 (w), 1132 (m), 1021 (m), 1000 (m), 860 (w), 840 (m), 815 (s), 770 (s), 740 (m). $C_{22}H_{10}O_3$ (322.3) calcd.: C 81.98 H 3.12 found: C 81.69 H 3.24.

Example 4

0.40 g (1.3 mmol) of perylene-3,4-dicarboximide is suspended in 25 ml of abs. methanol and then 0.19 g (3.5 mmol) of sodium methylate is added and the mixture is stirred at room temperature for 2 h with the exclusion of moisture. After stripping off the methanol on a rotary evaporator, there are added 20 ml of N-methylpyrrolidone as solvent and 1.13 g (4.03 mmol) of 1-bromotetradecane, and this suspension is then stirred for 24 h at room temperature. After the reaction is complete, the N-methylpyrrolidone and excess 1-bromo-tetradecane are removed by distillation under vacuum.

The reddish-brown residue is then suspended in 60 ml of tert-butanol, charged with 1.5 g (22.8 mmol) of KOH pellets and boiled for 3 h, the colour of the mixture changing from reddish-brown to yellowish-brown. After the reaction is complete, the tert-butanol is removed by distillation and the residue is suspended in water and acidified with conc. hydrochloric acid. To make the resulting brown residue agglomerate, the mixture is boiled for some time. The precipitate is collected by suction and washed with hot water. The residue is boiled with 2N potassium carbonate solution and is then washed with hot water until the filtrate runs colourless. The residue consists of unreacted perylene-3,4-dicarboximide and small amounts of N-tetradecyl-perylene-3,4-dicarboximide and can be recycled as starting product.

The filtrate is acidified with hydrochloric acid and is then filtered, giving 240 mg (60%) of brownish-red perylene-3,4-dicarboxylic acid anhydride.

IR (KBr): $\nu$=1780 cm$^{-1}$ (w), 1750 (m, C=O), 1725 (m, C=O), 1589 (s), 1568 (m), 1339 (m), 1280 (s), 1130 (m), 1020 (m), 1002 (m), 860 (w), 843 (m), 812 (s), 767 (s), 740 (m).

Example 5

1.29 g (4 mmol) of perylene-3,4-dicarboximide and 0.56 g (14.7 mmol) of sodium methylate are suspended in 50 ml of ethanol and the mixture is stirred for 5 h at room temperature. After removing the solvent by evaporation under reduced pressure, 50 ml of N-methyl-pyrrolidone and 1.01 ml of methyl iodide are added and the mixture is stirred for 2 h at room temperature. The solvent is removed by distillation under reduced pressure and the residue is washed with 100 ml of sulfuric acid (20%) and is then collected by suction and dried at 130° C. under reduced pressure, giving 1.17 g (87%) of red N-methylperylene-3,4-dicarboximide. IR (KBr): $\nu$=1692 cm$^{-1}$ (s), 1657 (s), 1570 (s), 1361 (s), 1238 (m), 810 (s), 748 (m). $C_{23}H_{13}O_2N$ (335,36) cacld.: C 82.37 H 3.91 N 4.18 found: C 81.71 H 4.01 N 3.98

The product is charged with 6.0 g of KOH pellets and 100 ml of tert-butyl alcohol and is then refluxed for 5 h. After cooling to room temperature, 100 ml of phosphoric acid (30%) are added and the mixture is heated for 15 min. The precipitate is collected by suction, washed with water and boiled for 30 min with 200 ml of 2N potassium carbonate solution. The hot solution is collected by suction from the undissolved components and is washed with hot water until the filtrate runs colourless. The hot filtrate is charged with 100 ml of acetic acid (50%), the brown residue is collected by suction and the resultant brown perylene-3,4-dicarboxylic acid anhydride is dried under reduced pressure at 130° C.

Yield: 0.73 g (56%) of a brown powder

IR (KBr): $\nu$=1750 cm$^{-1}$ (s), 1726 (s), 1591 (s), 1569 (s), 1340 (s), 1283 (s), 1131 (m), 1021 (m), 810 (m), 742 (m) $C_{22}H_{10}O_3$ (322,32) calcd.: C 81.98H 3.13 found: C 80.71H 3.39

Example 6

1.29 g (4 mmol) of perylene-3,4-dicarboximide and 1.35 g (12 mmol) of potassium-tert-butylate are suspended in 100 ml of ethanol and the mixture is refluxed for 2 h. After removing the solvent by evaporation under reduced pressure, 100 ml of N-methylpyrrolidone are added and the mixture is heated to 95° C. Subsequently, 1.82 ml (16 mmol) of benzyl chloride are added and the mixture is heated, with vigorous stirring, for 30 min to 120° C. The solvent is removed by distillation under reduced pressure and the residue is charged with 6.0 g of KOH pellets and 100 ml of tert-amyl alcohol and is then refluxed for 3 h. After cooling to room temperature, 100 ml of acetic acid (50%) are added and the mixture is heated for 1 hour to make it easier to filter the precipitate. The precipitate is collected by suction, washed with water and is then boiled for 30 min with 100 ml of 2 N potassium carbonate solution. The hot solution is collected by suction from the undissolved components and is washed with hot water until the filtrate runs colourless. The hot filtrate is charged with 100 ml of acetic acid (50%), the brown precipitate is collected by suction and the resultant brown perylene-3,4-dicarboxylic acid anhydride is dried under reduced pressure at 130° C.

Yield: 0.47 g (37%)

IR (KBr): $\nu$=1752 cm$^{-1}$ (s), 1725 (s), 1591 (s), 1569 (s), 1341 (s), 1283 (s), 1131 (m), 1020 (m), 810 (m), 741 (m) $C_{22}H_{10}O_3$ (322.32), calcd.: C 81.98 H 3.13; found: C 81.22 H 3.42

Example 7

1.29 g (4 mmol) of perylene-3,4-dicarboximide and 1.35 g (12 mmol) of potassium-tert-butylate are suspended in 100 ml of ethanol and the mixture is refluxed for 1 h. After removing the solvent by evaporation under reduced pressure, 100 ml of N-methylpyrrolidone are added and the mixture is heated to 95° C. Subsequently, 1.82 ml (16 mmol) of benzyl chloride are added and the mixture is heated, with vigorous stirring, for 50 min to 120° C. The solvent is removed by distillation under reduced pressure and the residue is charged with 5.1 g of KOH pellets and 100 ml of tert-butyl alcohol and refluxed for 2 h 30 min. After cooling to room temperature, 50 ml of sulfuric acid (30%) and 50 ml of water are added and the mixture is heated for 1 hour to make it easier to filter the precipitate. The precipitate is collected by suction, washed with water and is then boiled for 1 h 30 min with 100 ml of 2N potassium carbonate solution. The hot solution is collected by suction from the undissolved components and is washed with hot water until the filtrate runs colourless. The hot filtrate is charged with 100 ml of acetic acid (50%), the brown precipitate is collected by suction and the resultant brown perylene-3,4-dicarboxylic acid anhydride is dried under reduced pressure at 130° C.

Yield: 0.31 g (24%)

IR (KBr): ν=1750 cm$^{-1}$ (s), 1722 (s), 1591 (s), 1569 (s), 1341 (s), 1283 (s), 1131 (m), 1019 (m), 810 (m), 741 (m)

Example 8

1.29 g (4 mmol) of perylene-3,4-dicarboximide and 1.80 g (16 mmol) of potassium-tert-butylate are suspended in 100 ml of tert-amyl alcohol and the mixture is refluxed for 30 min. Subsequently, 2.30 ml (20 mmol) of benzyl chloride are added and the mixture is refluxed for 7 h. After removing the solvent by distillation under reduced pressure, the residue is charged with 100 ml of phosphoric acid (30%) and collected by suction. The residue is charged with 8.0 g of KOH pellets and 100 ml of tert-amyl alcohol and is refluxed for 4 h 30 min. After cooling to room temperature, 100 ml of sulfuric acid (30%) are added. The solvent is removed by distillation under reduced pressure and the precipitate is collected by suction, washed with water and is then boiled for 45 min with 100 ml of 2N potassium carbonate solution. The solution is collected by suction from the undissolved components and is washed with hot water until the filtrate runs colourless. After adding 50 ml of sulfuric acid (30%), the precipitated residue is collected by suction and dried under reduced pressure at 130° C.

Yield: 0.14 g (11%)

IR (KBr): ν=1755 cm$^{-1}$ (s), 1725 (s), 1591 (s), 1569 (s), 1341 (s), 1284 (s), 1141 (m), 1284 (m), 1019 (m), 810 (m), 741 (m)

Example 9

1.29 g (4 mmol) of perylene-3,4-dicarboximide and 0.90 g (8 mmol) of potassium-tert-butylate are suspended in 100 ml of 2-methoxyethanol and the mixture is stirred for 1 h at 70 ° C. After removing the solvent by evaporation under reduced pressure, 120 ml of N-methylpyrrolidone and 0.95 ml (10 mmol) of dimethyl sulfate are added and the mixture is stirred for 4 h 30 min at 70 ° C. The solvent is removed by distillation under reduced pressure and the residue is charged with 8.0 g of KOH pellets and 100 ml of tert-butyl alcohol and is then refluxed for 14 h. After cooling to room temperature, 100 ml of phosphoric acid (30%) are added. The solvent is removed by evaporation under reduced pressure and the precipitate is collected by suction, washed with water and is then boiled for 30 min with 200 ml of 2N potassium carbonate solution. The solution is collected by suction from the undissolved components and 150 ml of phosphoric acid (30%) are then added to the solution. The mixture is heated for 15 min. and the precipitated residue is then collected by suction and dried under reduced pressure at 130° C.

Yield: 0.29 g (22%)

IR (KBr): ν=1750 cm$^{-1}$ (s), 1724 (s), 1591 (s), 1569 (s), 1341 (s), 1283 (s), 1131 (m), 1019 (m), 997 (m), 810 (m), 741 (m) C$_{22}$H$_{10}$O$_3$ (322.32) calcd.: C 81.98 H 3.13 found: C 80.34 H 3.38

What is claimed is:

1. A process for the preparation of perylene-3,4-dicarboxylic acid anhydrides of the formula I

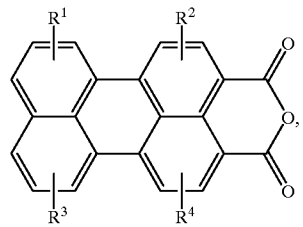

wherein R$^1$, R$^2$, R$^3$ and R$^4$ can each be independently of one another hydrogen, halogen, C$_1$–C$_{20}$alkyl, C$_3$–C$_{14}$cycloalkyl, C$_1$–C$_{20}$alkoxy, phenyl, phenyloxy or phenylthio, where phenyl can in each case be mono- or polysubstituted by halogen, C$_1$–C$_{20}$alkyl, C$_3$–C$_{14}$cycloalkyl and/or C$_1$–C$_{20}$alkoxy; —NR$^5{}_2$ or —OR$^5$, wherein R$^5$ is hydrogen or C$_1$–C$_{20}$alkyl, or one of the pairs R$^1$/R$^2$ and R$^3$/R$^4$ each in 6,7- or 1,12-position is a bridge having the bridge atoms or bridge atom groups —O—, —S—, S=O, SO$_2$ or —NR$^6$, wherein R$^6$ is hydrogen, C$_1$–C$_{20}$alkyl or C$_3$–C$_{14}$cycloalkyl, by treating a perylene-3,4-dicarboximide of formula II

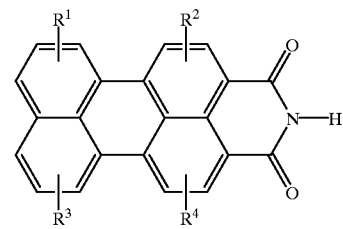

(a) in a first step with a base and, (b) in a second step, reacting the resultant anion with an alkylation agent R$^7$—X, X being halogen and R$^7$ being unsubstituted or phenyl-substituted C$_1$–C$_{20}$alkyl, to the corresponding carboximide and, (c) in a third step, treating the alkylated carboximide first with a base and, after the treatment with a base, obtaining the perylene-3,4-dicarboxylic acid anhydride I by acidifying the reaction mixture.

2. A process according to claim 1, wherein the base used in the first step (a) is an alkali metal salt of a C$_1$–C$_4$alkanol or an alkali metal hydroxide or alkaline earth metal hydroxide.

3. A process according to claim 1, wherein the alkylation agent is dimethyl sulfate, C$_1$–C$_6$alkyl bromide, C$_1$–C$_6$alkyl iodide or benzyl chloride.

4. A process according to claim 1, which comprises carrying out each of the reactions of steps (a) to (c) in a solvent.

* * * * *